United States Patent [19]

Mehmanpazir et al.

[11] Patent Number: 5,776,065
[45] Date of Patent: Jul. 7, 1998

[54] APPARATUS AND METHOD FOR CONTROLLING AN ULTRASOUND TRANSDUCER ARRAY

[75] Inventors: Behnam Mehmanpazir, Sunnyvale; John D. Marshall, Redwood City; Michael Hazarian, San Jose, all of Calif.

[73] Assignee: Acuson Corporation, Mountain View, Calif.

[21] Appl. No.: 716,504

[22] Filed: Sep. 18, 1996

[51] Int. Cl.[6] .................................................. A61B 8/00
[52] U.S. Cl. .................................................. 600/437; 600/459
[58] Field of Search .................... 128/660.01, 660.1, 128/902, 662.03; 601/2, 3, 4; 600/437, 459

[56] References Cited

U.S. PATENT DOCUMENTS

| | | |
|---|---|---|
| 4,726,230 | 2/1988 | Yoshikawa et al. .................. 73/607 |
| 4,811,740 | 3/1989 | Ikeda et al. . |
| 4,843,232 | 6/1989 | Emo et al. . |
| 5,318,027 | 6/1994 | Fukui . |
| 5,403,980 | 4/1995 | Eckrich . |
| 5,410,148 | 4/1995 | Barron, Jr. et al. .................. 250/221 |
| 5,446,775 | 8/1995 | Wright et al. . |
| 5,505,203 | 4/1996 | Deitrich et al. . |
| 5,542,425 | 8/1996 | Marshall et al. .................. 128/660.01 |

*Primary Examiner*—Francis Jaworski
*Attorney, Agent, or Firm*—Brinks Hofer Gilson & Lione

[57] ABSTRACT

A transducer array control system for use with a transducer housing and a transducer array that includes a sensing mechanism that generates a sensor signal having a first state indicative of the use of the transducer array. A control mechanism generates a transducer disabling signal when the sensor signal fails to enter the first state within a selected time period. Methods for disabling a transducer array are also provided.

20 Claims, 3 Drawing Sheets

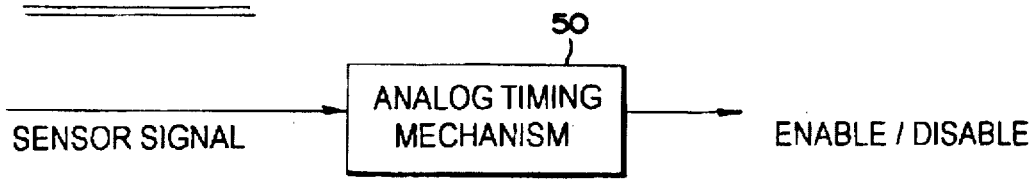
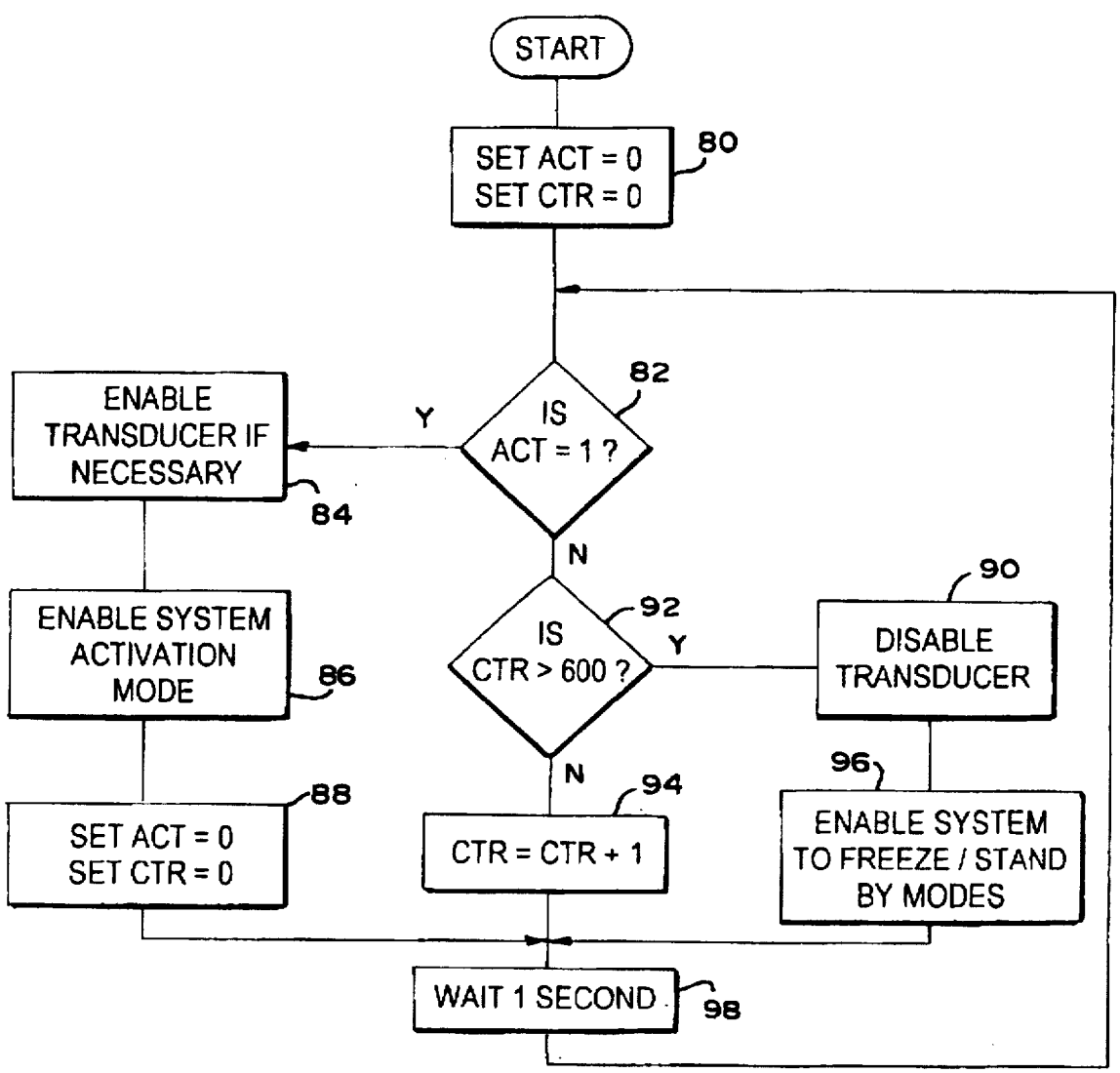

APPARATUS AND METHOD FOR CONTROLLING AN ULTRASOUND TRANSDUCER ARRAY

BACKGROUND OF THE INVENTION

The present invention relates to an ultrasound imaging system. More particularly, the present invention relates to an apparatus and method for disabling an ultrasound transducer when not in use with a patient.

Through the use of an ultrasound probe, a sonographer can obtain an image of a region of a patient's body. In the probe, a number of acoustic piezoelectric transducer elements are electrically excited by an ultrasound control and operating system to obtain an image of the tissue that the probe is being applied against. Prior to the use of the probe, an acoustical gel is applied to the probe and to the skin of a patient in order to increase acoustical coupling. Generally, the acoustical gel is a thin film of a water-based material.

One problem associated with the use of piezoelectric transducer elements is that they are not completely energy efficient, and the temperature of these elements can increase to an undesirable level under certain conditions. In particular, the temperature of the probe generally does not exceed a preferred level while in use, because any heat generated is conducted away from the probe by the acoustical gel and the body of the patient. However, the temperature of the probe can increase to an undesirable level if the transducer is left activated and the probe housing is not in contact with the body of the patient. This may happen, for example, if a sonographer fails to disable the transducer array within the probe after the end of an examination.

If the temperature of the probe is allowed to exceed a certain temperature level, e.g. 41° C., certain problems may result. For example, if a probe were allowed to reach or exceed this temperature, there is a risk that a patient's skin could be burned if the sonographer reinitiated an examination under these conditions. In addition, the transducer elements themselves can be adversely affected when subject to excessive temperatures. Therefore, it is desirable to control the temperature of the transducers and the probe.

Some devices that allow the sonographer to measure the temperature of the probe are known. For example, it is known that a temperature sensor can be incorporated into the tip of a transesophageal probe. The sensor can instruct the control system for the probe to produce a warning signal or to terminate activation of the transducers if the probe temperature exceeds safe levels. One disadvantage of this device is that the probe is allowed to reach an undesirable temperature level before the transducers are disabled. A further disadvantage of this device is the added cost and complexity of manufacturing a probe including a temperature sensor in the relatively small space that forms the tip.

Therefore, an improved apparatus and method for controlling the an ultrasound probe are needed.

SUMMARY OF THE INVENTION

According to a first aspect of this invention, a transducer array control system is provided for use with a transducer housing and a transducer array. The control system includes a sensing mechanism that generates a sensor signal having a first state indicative of the use of the transducer array. A control mechanism generates a transducer disabling signal when the sensor signal fails to enter the first state within a selected time period.

According to another aspect of the present invention, an ultrasound probe for use with an ultrasound control system is provided. The ultrasound probe includes a sensing mechanism attached to the transducer housing. The sensing mechanism generates a sensor signal indicative of the use of the probe. A control mechanism responsive to the sensor signal is also provided. The control mechanism generates a transducer enabling signal when the sensor signal generates a sensor signal having a first state indicative of use of the probe.

According to a further aspect of the invention, a method of controlling an ultrasound transducer array is provided. The method includes the step of generating a sensor signal in response to the use of a transducer. The method also includes the step of generating a transducer disabling signal when the sensor signal is not detected within a selected time period.

In the preferred embodiments discussed below, several sensing mechanisms are disclosed, including a touch-sensitive sensing mechanism and a mechanical sensing mechanism. In addition, several preferred timing mechanisms are also disclosed herein. These embodiments allow the disclosed system and method to disable a transducer array when it is not being used by a sonographer. In this way, the transducer array can be disabled before it exceeds an undesirable temperature level. In addition, the transducer array can be reenabled when in use at a later time.

The present invention will be best understood by reference to the following detailed description taken in conjunction with the accompanying drawings.

BRIEF DESCRIPTION OF THE DRAWINGS

FIG. 4 is a block diagram showing another embodiment of a timing mechanism; and

FIG. 5 is a flow chart showing a further preferred embodiment of a timing mechanism.

DETAILED DESCRIPTION OF THE PRESENTLY PREFERRED EMBODIMENTS

The following discussion is first directed to the system in general, and then turns to a more detailed discussion of the preferred embodiments of the individual components.

As used herein, the term "sensing mechanism" is intended to be construed broadly to encompass any of the disclosed sensing mechanisms together with other known sensing mechanisms that detect the use of the probe, e.g., the touch of a sonographer's hand on the probe or the movement of the probe.

As also used herein, the term "timing mechanism" is intended to be construed broadly to encompass any of the disclosed timing mechanisms together with other timing mechanisms known to the art.

System Overview

Figure 1:
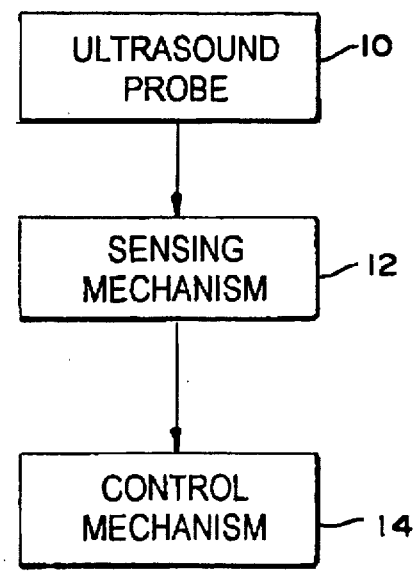
FIG. 1 is a block diagram that illustrates one embodiment of the present invention.

FIG. 1 is a block diagram that generally illustrates one preferred embodiment of the present invention. This embodiment includes an ultrasound probe 10 having a transducer array, a sensing mechanism 12, and a control mechanism 14. The probe 10 and sensing mechanism 12 may be of the type shown in FIGS. 2A and 2B, i.e., a standard ultrasonic probe having a touch-sensitive sensing mechanism. The control mechanism 14 includes a timing mechanism that may be of the type shown in FIGS. 3–5, i.e., an analog, a digital or a programmable timing mechanism.

The sensing mechanism 12 generates a sensor signal having a first state that is indicative of the use of the probe 10. Alternatively, when the probe 10 is not in use, the sensing mechanism 12 does not generate such a sensor signal. Once initiated, the control mechanism 14 checks to determine if the sensing mechanism 12 is producing a signal indicative of the use of the probe 10. Once a sensor signal has been detected that is indicative of the use of the probe 10, the control mechanism 14 generates a signal to enable the transducer array. The control mechanism 14 then continues to check if a sensor signal indicative of the use of the probe 10 is being produced.

The control mechanism 14 includes a timing mechanism that measures a selected time period. During the time period that the sensing mechanism 12 generates a sensor signal indicative of the use the probe 10, the timing mechanism is reset. Once the sensing mechanism 12 fails to generate a signal indicative of the use of the probe 10, the timing mechanism is not reset. The control mechanism 14 then continues to check if a sensor signal indicative of the use of the probe 10 is detected at a later time. Furthermore, the control mechanism 14 checks the timing mechanism to determine if a selected time period has elapsed.

If a sensor signal indicative of the use of the probe 10 is not detected within the selected time period, the control mechanism 14 provides a signal that disables the transducer array. Accordingly, when the probe 10 has not been used within the selected time period, the transducer array will be disabled.

Once the sensing mechanism 12 again generates a signal indicative of the use the probe 10, the control mechanism 14 generates a signal to reenable the transducer array. As described above, the transducer array will then be disabled once the probe 10 has not been used within the selected time period.

Preferably, the selected time period is chosen so that the probe 10 does not overheat. As those of ordinary skill in the art will recognize, the selected time period may vary depending on the type of ultrasound control system or probe, e.g., a transesophageal probe or an endocavity probe.

The Sensing Mechanism

Figure 2A:
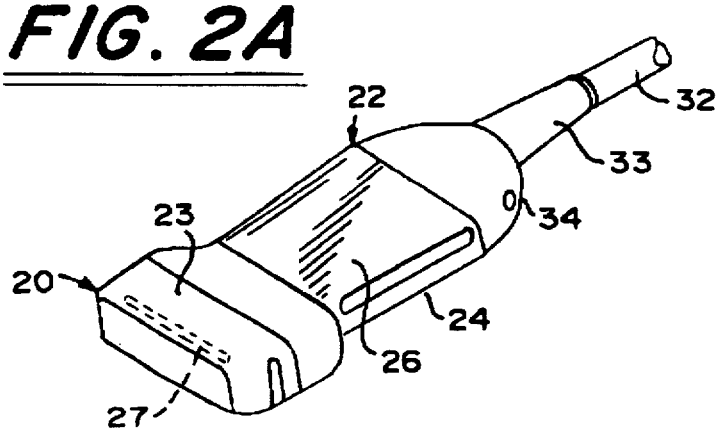
FIGS. 2A and 2B are perspective views of two ultrasound probes having sensing mechanisms in accordance with one preferred embodiment of the present invention.
Figure 2B:
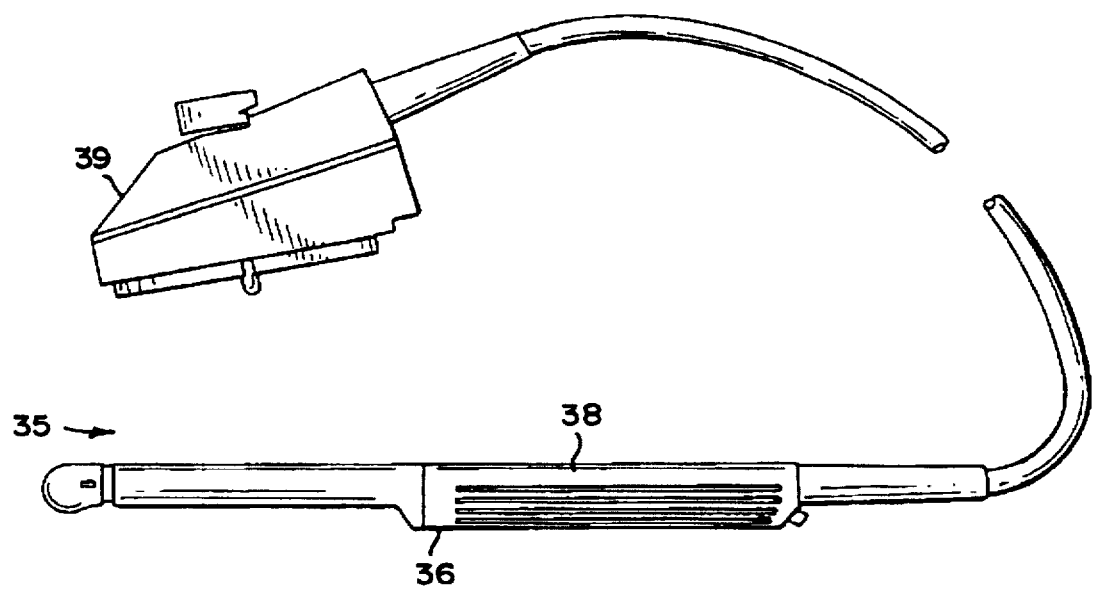

FIGS. 2A and 2B are perspective views of ultrasound probes including sensing mechanisms in accordance with a presently preferred embodiment of the present invention. As shown in FIG. 2A, the ultrasound probe 20 includes an transducer housing 22 that includes a nose piece 23 and a grip portion 24. The grip portion 24 is designed to fit against the hand of the sonographer. According to the preferred embodiment of the invention, a touch-sensitive mechanism 26 is located in the grip portion 24. A plurality of ultrasound transducers 27 are mounted in the nose piece 23. An electrical cable 32 and strain relief 33 extend from the rear portion 34 of the transducer housing 22. The electrical cable 32 is connected to an ultrasound control system (not shown).

A second ultrasound probe 35 is shown in FIG. 2B. The second ultrasound probe 35 is designed for endocavity use. A touch-sensitive mechanism 36 is similarly located in the hand-grip area 38 of the probe 35. A connector 39 is used to provide a connection with the ultrasound control system.

In the embodiments shown in FIGS. 2A and 2B, touch-sensitive mechanisms 26, 36 may be implemented in a manner known in the art. In such known arrangements, the output of a touch-sensitive capacitor will vary when a human hand is placed in close proximity to one of the capacitor plates. For example, a voltage will be produced because of a change in the capacitance of the capacitor. According to one embodiment, a touch-sensitive capacitor is connected to an L-C circuit and a transistor. The operation of the L-C circuit is used to produce an oscillating output from the collector of the transistor when the capacitor is not in contact with a human hand. The transistor, however, will produce a constant voltage whenever the touch-sensitive capacitor plate is in close proximity to a human hand. For a more detailed description of a touch-sensitive capacitor, reference is made to the touch-sensitive capacitor disclosed in U.S. Pat. No. 5,410,148, issued to Barron, et al., the disclosure of which is hereby incorporated by reference.

Other known sensing mechanisms may also be used. For example, a mechanical switch may be attached to the transducer housing 22. One preferred mechanism includes positioning the switch in the grip area 24. A sonographer would hold the switch down thereby producing a signal indicating that the probe is in use. Another alternative involves the use of a commonly known motion sensor or acceleration-sensitive switch. An acceleration-sensitive switch includes, for example, a mass connected to a deformable spring that completes an electrical path between two terminals when the probe is accelerated, i.e., is in use.

Another preferred embodiment of the sensing mechanism includes the use of a conductive ink pattern. A conductive ink pattern may be formed over a dielectric substrate, and the pattern may be electrically coupled to a circuit that places a small voltage across the pattern. When a user touches the ink pattern, the voltage across the pattern changes. By detecting a change in the voltage across the ink pattern, the control mechanism may determine that the probe is still in use. One example of a conductive ink pattern and circuit is shown in U.S. Pat. No. 5,403,980, issued to Eckrich, the disclosure of which is hereby incorporated by reference.

A further preferred embodiment of the sensing mechanism includes the use of an electro-optical sensing mechanism. One example of an electro-optical sensing mechanism is disclosed in U.S. Pat. No. 4,843,232, issued to Emo et al., the disclosure of which is hereby incorporated by reference.

The particular sensing mechanism chosen should be carefully designed to respond only to the use of the probe. For example, the capacitance of the touch-sensitive embodiment should be selected so as to respond only to the touch of a human hand. In the alternative, the output of the sensing mechanism can be checked for changes over time in order to avoid any improper indication of the use of the probe.

The Timing Mechanism

Various timing mechanisms may be used to measure the selected time period. In one preferred embodiment, the selected time period is substantially within the range of 1–10 minutes. More preferably, the selected time period is substantially within the range of 5–10 minutes. Most preferably, the selected time period is substantially within the range of 9–10 minutes.

Figure 3:
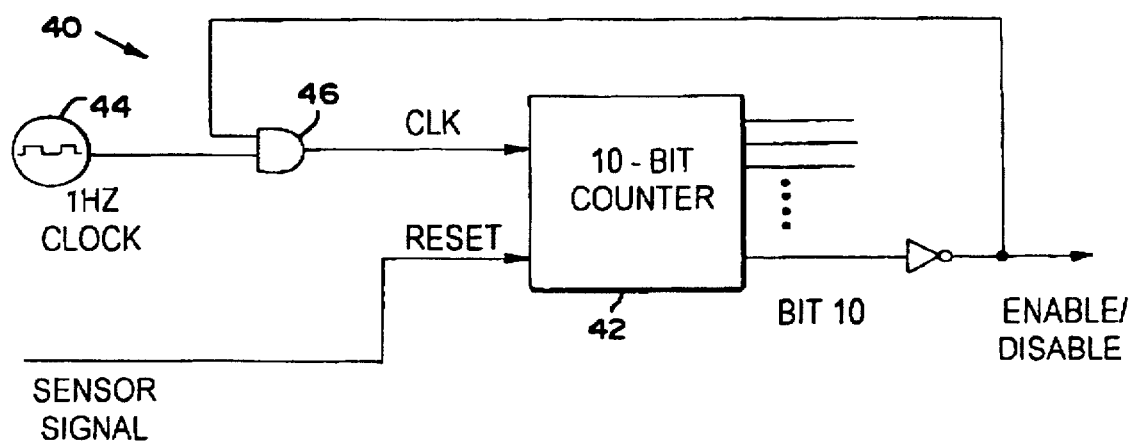
FIG. 3 is a circuit diagram showing one embodiment of a timing mechanism.

In accordance with one preferred embodiment as shown in FIG. 3, a digital circuit 40 is implemented. Using a 10-bit counter 42 and a 1 Hz clock 44, a time period of 512 seconds may be measured. The 10-bit counter 42 is reset if a sensor signal indicative of the use of the probe 10 is being produced. If a sensor signal is not received within a period of 512 seconds, the output of bit-10 will produce a signal indicating that the selected time period has elapsed. As a result, the controller 14 will produce a signal to disable the transducer array. The output of bit-10 is also input to an AND gate 46 to disable the counter 42 until a subsequent sensor signal indicative of the use of the probe 10 is produced by the sensing mechanism 12. Once a subsequent sensor signal is detected, a signal is produced to again enable the transducer array. The clock 44 is then no longer blocked from the counter 42 by the AND gate 46.

As shown in the block diagram in FIG. 4, an analog timing mechanism 50 may also be used. An example of a known analog timing mechanism includes the use of a resistor, a capacitor and an integrated circuit timer as available from National Semiconductor under part no. LM 555. As known to those of ordinary skill in the art, the time delay for the analog timing mechanism may be chosen by the selecting the resistance and capacitance of the particular circuit elements.

While digital, analog or hybrid circuitry may be used to measure the selected time period, the preferred embodiment includes a timing mechanism that is implemented in the software. A flow chart for a suitable routine is illustrated in FIG. 5. It will be recognized that this routine may be modified, as appropriate, in order to run on any suitable computer, processor or controller.

As shown in FIG. 5, an activation detector register and a counter are set to "0" (step 80). The activation detector register is set to "1" when a sensor signal indicative of the use of the probe 10 is detected. The system proceeds to check if a sensor signal indicative of the use of the probe 10 has been detected (step 82).

If a sensor signal indicative of the use of the probe 10 is detected, the transducer array is enabled (step 84) and system is placed in the activation mode (step 86). These steps 84 and 86 will not be necessary if the transducer array has not been previously disabled and the system placed in the freeze/stand-by mode, as described below. The activation detector register and counter are then reset to "0" (step 88) indicating that the probe 10 is in use.

After a one second delay (step 90), the system again checks to determine if a sensor signal indicative of the use of the probe has been detected (step 82). If a sensor signal indicative of the use of the probe 10 has not been detected, a counter register is polled to determine if a count of 600 (ten minutes) has been exceeded (step 92). If not, a count is added to the counter register (step 94). After a one second delay (step 90), the activation detector register is again checked to determine if a sensor signal indicative of the use of the probe 10 has been produced. If a such a sensor signal is not detected, the counter register is again polled to determine if a count of 600 has been exceeded (step 92). If a count of 600 has been exceeded, this indicates that the probe 10 has not been used within the preceding ten minutes. The control system 14 then disables the transducer array (step 90) and the system is placed in the freeze/stand-by mode (step 92). Once a subsequent sensor signal is detected, the system proceeds through steps 84 and 86, as described above, to reenable the transducer array.

The present invention also includes a method of controlling an ultrasound transducer. This method includes the step of generating a sensor signal in response to the use of the transducer. This method also includes the step of generating an ultrasound transducer disabling signal when the sensor signal is not detected within a selected time period.

A further method of controlling an ultrasound transducer is also provided. This method includes the step of generating a sensor signal in response to the use of a transducer. This method also includes the steps of running a timing mechanism and resetting the timing mechanism when the sensor signal is in a selected state indicative of the use of the transducer. This method further includes the step of generating a transducer disabling signal when the timing mechanism is not reset within a selected time period.

The present invention provides the advantage of disabling the transducer array when not in use in order to prevent overheating of the probe. Therefore, a sonographer's use of an overheated probe should be avoided. In addition, the transducer array will not be subject to the deleterious effects associated with excessive temperatures.

The present invention also provides the advantage of activating a transducer based on the use of the probe. This advantage is useful because it provides an easy method of activating a transducer array. This advantage is particularly useful in a system having a plurality of different probes that are designed to image particular body parts. In particular, this system includes a plurality of probes that are enabled based on the use of a particular probe. In addition to producing a signal indicative of the use of the particular probe, the sensing mechanism would also produce a signal that identifies which probe was in use.

It is intended that the foregoing detailed description be regarded as illustrative rather than limiting, and it is understood that the following claims, including all equivalents, are intended to define the scope of the invention.

We claim:

1. In combination with a transducer housing and an ultrasound transducer array mounted in the transducer housing, a transducer array control system comprising:
   a sensing mechanism that generates a sensor signal, the sensor signal having a first state indicative of use of the transducer array; and
   a control mechanism responsive to the sensor signal, the control mechanism generating a transducer disabling signal when the sensor signal fails to enter the first state within a selected time period.

2. The transducer array control system of claim 1 wherein the sensing mechanism comprises a touch-sensitive mechanism.

3. The transducer array control system of claim 2 wherein the touch-sensitive mechanism comprises a capacitance sensor.

4. The transducer array control system of claim 1 wherein the sensing mechanism comprises a mechanical switch.

5. The transducer array control system of claim 1 wherein the control mechanism comprises an analog timing mechanism that measures the selected time period.

6. The transducer array control system of claim 1 wherein the control mechanism comprises a digital timing mechanism that measures the selected time period.

7. The transducer array control system of claim 1 wherein the control mechanism comprises a programmable timing mechanism that measures the selected time period.

8. The transducer array control system of claim 7 wherein the selected time period is substantially within the range of 1-10 minutes.

9. An ultrasound probe for use with an ultrasound control system comprising;
   a transducer housing;
   a sensing mechanism attached to the transducer housing, the sensing mechanism generating a sensor signal having a first state indicative of use of the probe; and
   a control mechanism responsive to the sensor signal, the control mechanism generating a transducer enabling signal when the sensor signal generates a sensor signal having a first state indicative of use of the probe.

10. The ultrasound probe of claim 9 wherein the sensing mechanism is attached to the grip portion of the transducer housing.

11. The ultrasound probe of claim 10 wherein the sensing mechanism comprises a touch-sensitive mechanism.

12. The ultrasound probe of claim 11 wherein the touch-sensitive mechanism comprises a capacitance sensor.

13. A method of controlling an ultrasound transducer array, the method comprising the following steps:

generating a sensor signal in response to use of the transducer; and generating a transducer disabling signal when the sensor signal is not detected within a selected time period.

14. The method of claim 13 further comprising the step of removing the transducer disabling signal when a sensor signal indicative of use of the transducer is detected.

15. The method of claim 14 wherein the sensing mechanism comprises a touch-sensitive mechanism.

16. The method of claim 15 wherein the selected time period is substantially within the range of 1–10 minutes.

17. A method of controlling an ultrasound transducer array, the method comprising the following steps:

generating a sensor signal in response to the use of a transducer;

running a timing mechanism;

resetting the timing mechanism when the sensor signal is in a selected state indicative of use of the transducer; and generating a transducer disabling signal when the timing mechanism is not reset within a selected time period.

18. The method of claim 17 further comprising the step of removing the transducer disabling signal when the sensor signal is in a second selected state indicative of use of the transducer.

19. The method of claim 18 wherein the sensing mechanism comprises a touch-sensitive mechanism.

20. The method of claim 19 wherein the timing mechanism comprises a programmable timing mechanism.

* * * * *

UNITED STATES PATENT AND TRADEMARK OFFICE
CERTIFICATE OF CORRECTION

Page 1 of 2

PATENT NO. : 5,776,065
DATED : July 7, 1998
INVENTOR(S) : Mehmanpazir et al.

It is certified that error appears in the above-identified patent and that said Letters Patent is hereby corrected as shown below:

In column 1, line 55, delete "the".

In column 3, line 21, after "use" insert --of--.

In column 3, line 36, after "use" insert --of--.

In column 3, line 51, change "an" to --a--.

In column 5, line 16, after "555." insert two spaces.

In column 5, line 18, delete "the" (first occurrence).

In column 5, line 34, after "and" insert --the--.

In column 5, line 48, change "(step 90)" to --(step 98)--.

UNITED STATES PATENT AND TRADEMARK OFFICE
CERTIFICATE OF CORRECTION

PATENT NO. : 5,776,065
DATED : July 7, 1998
INVENTOR(S) : Mehmanpazir, et. al.

It is certified that error appears in the above-identified patent and that said Letters Patent is hereby corrected as shown below:

In column 5, line 57, change "(step 92)" to -- (step 96) --.

Signed and Sealed this

Eighth Day of February, 2000

*Attest:*

Q. TODD DICKINSON

*Attesting Officer*   Commissioner of Patents and Trademarks